(12) United States Patent
Sekido et al.

(10) Patent No.: US 8,414,634 B2
(45) Date of Patent: Apr. 9, 2013

(54) ELONGATE MEDICAL DEVICE

(75) Inventors: Aya Sekido, Ashigarakami-gun (JP); Takeshi Kanamaru, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 695 days.

(21) Appl. No.: 11/878,857

(22) Filed: Jul. 27, 2007

(65) Prior Publication Data

US 2008/0027482 A1   Jan. 31, 2008

(30) Foreign Application Priority Data

Jul. 28, 2006  (JP) .................................. 2006-206962
May 17, 2007  (JP) .................................. 2007-132187

(51) Int. Cl.
*A61F 2/06* (2006.01)
(52) U.S. Cl. ...................................................... 623/1.11
(58) Field of Classification Search .................. 606/106, 606/108, 200; 623/1.11; 335/296, 219, 281, 335/282, 297; 600/11, 12, 13
See application file for complete search history.

(56) References Cited

U.S. PATENT DOCUMENTS

| | | | | |
|---|---|---|---|---|
| 2,979,655 A | * | 4/1961 | De Forest ..................... | 324/213 |
| 3,243,755 A | * | 3/1966 | Johnston ...................... | 439/825 |
| 5,353,807 A | * | 10/1994 | DeMarco ..................... | 600/585 |
| 5,725,546 A | * | 3/1998 | Samson ........................ | 606/191 |
| 5,766,160 A | * | 6/1998 | Samson et al. .................... | 606/1 |
| 5,891,128 A | * | 4/1999 | Gia et al. .......................... | 606/1 |
| 5,895,385 A | * | 4/1999 | Guglielmi et al. .............. | 606/32 |
| 6,375,606 B1 | * | 4/2002 | Garibaldi et al. ............... | 600/12 |
| 6,603,994 B2 | * | 8/2003 | Wallace et al. ............... | 600/434 |
| 6,745,079 B2 | * | 6/2004 | King ............................ | 607/117 |
| 2004/0002643 A1 | | 1/2004 | Hastings et al. | |
| 2005/0192620 A1 | * | 9/2005 | Cully et al. ................... | 606/200 |
| 2006/0206140 A1 | | 9/2006 | Shaolian et al. | |
| 2006/0282112 A1 | * | 12/2006 | Griffin ......................... | 606/200 |
| 2007/0141099 A1 | * | 6/2007 | Buiser et al. .................. | 424/422 |

FOREIGN PATENT DOCUMENTS

| | | |
|---|---|---|
| JP | 7-265431 A | 10/1995 |
| JP | 10-512160 A | 11/1998 |

* cited by examiner

*Primary Examiner* — Gary Jackson
*Assistant Examiner* — Jonathan Hollm
(74) *Attorney, Agent, or Firm* — Buchanan Ingersoll & Rooney PC

(57) ABSTRACT

An elongate medical body for implanting an embolic coil at a desired position, or retrieving an embolic coil from an aneurysm, includes a flexible wire main body, and an electromagnet provided at a distal end portion of the wire main body. The electromagnet can generate a magnetic field at the distal end portion. An energization state of the electromagnet is switched to attach and detach a spiral embolic coil having a magnetically attractable proximal end portion to and from the distal end portion.

24 Claims, 9 Drawing Sheets

ELONGATE MEDICAL DEVICE

TECHNICAL FIELD

The subject matter of this application relates generally to an elongate medical device, and more particularly to an elongate medical device for supplying an embolic coil to an aneurysm of a blood vessel.

BACKGROUND DISCUSSION

In the past, aneurysms have been addressed by various treatment techniques such as the surgical resection of the aneurysm and the implantation of an artificial blood vessel (a tube made of an artificial material) at the resectioned region. As an alternative, so-called bypass surgery has been used in which another new blood vessel path is formed to secure blood in the past. However, generally speaking, patients who develop an aneurysm are generally aged or older persons. Undergoing a major surgery places a heavy burden on patients and can create difficulties in many cases. In addition, complications during or after the surgery are possible and carry risks.

Recently, another treatment technique (aneurysm embolization) has been developed in which an embolic material is percutaneously supplied to and filled in the aneurysm of a blood vessel from a femoral region or the like. This treatment technique provides an advantage of significantly reducing the risk of surgery and burden on the patient. Such a treatment technique uses an elongate medical body in which a coil-like embolic material (embolic coil) connected to the tip of the main body of an elongate body (see e.g., Japanese Patent Laid-open No. Hei 7-265431, hereinafter referred to as Patent Document 1).

When the elongate medical body in Patent Document 1 is used, it is percutaneously introduced into a blood vessel. Then, the tip of the elongate body is advanced to a target region or the position of the aneurysm of the blood vessel in the brain under X-ray illumination. High-frequency current is supplied to the aneurysm via the main body of the elongate body to thermally resect a joint between the main body of the elongate body and the embolic coil. Thus, the embolic coil is supplied to and filled in the aneurysm.

With the medical elongate body of Patent Document 1, however, if the joint between the main body of the elongate body and the embolic coil is resected and the embolic coil is once implanted, it is impossible to remove or recover the embolic coil. Because of this, if the embolic coil is not implanted at the desired position, it is necessary to recover the embolic coil by other ways and implant a new embolic coli, thus burdening the patient.

Additionally, when the joint between the main body of the elongate body and the embolic coil is resected, dissolved material or the like may flow into the living body from the joint, even though in minute amounts. From a safety standpoint, it is preferable to eliminate the outflow of such a material.

SUMMARY

There is a need for a way of implanting an embolic coil at a desired position while reducing a burden placed on a patient, and also retrieving such an embolic coil that has been positioned.

Disclosed here is a medical device and an elongate body for delivering a helical embolic coil.

A medical device for delivering a helical embolic coil into an aneurysm comprises a flexible elongate body possessing a distal end portion, an electromagnet disposed at the distal end portion of the elongate body, the electromagnet being energizable to generate a magnetic field at the distal end portion of the elongate body, a helical embolic coil made of ferromagnetic material and possessing a proximal end portion, the distal end portion of the elongate body being configured to receive the proximal end portion of the helical embolic coil, and to magnetically attract the proximal end portion of the helical embolic coil to secure the helical embolic coil to the distal end portion of the flexible elongate body and to release the proximal end portion of the helical embolic from the distal end portion of the flexible elongate body by changing an energization status of the electromagnet.

The proximal end portion of the embolic coil can be made of a ferromagnetic material, and the proximal end portion of the embolic coil is adapted to be magnetically attracted to the distal end portion of the elongate body to secure the embolic coil to the elongate body by energizing the electromagnet, with the proximal end portion of the embolic coil being released from magnet attraction to the distal end of the elongate body by discontinuing the energization of the electromagnet.

The proximal end portion of the embolic coil can be formed of ferromagnetic material, with the proximal end portion of the embolic coil being adapted to be magnetically attracted to the distal end portion of the elongate body to secure the embolic coil to the elongate body by energizing the electromagnet, and with the proximal end portion of the embolic coil being released from magnet attraction to the distal end of the elongate body by reversing polarity of the electromagnet relative to the polarity of the electromagnet when the proximal end portion of the embolic coil is magnetically attracted to the distal end portion of the elongate body.

The proximal end portion of the embolic coil can be formed of ferromagnetic material, with the proximal end portion of the embolic coil being adapted to be magnetically attracted to the distal end portion of the elongate body to secure the embolic coil to the elongate body by discontinuing energization of the electromagnet, and with the proximal end portion of the embolic coil being released from magnet attraction to the distal end of the elongate body by energizing the electromagnet.

At least a portion of the distal end portion of the elongate body can be configured as a tapered portion progressively reducing in outer diameter towards the distal end.

At least a portion of the proximal portion of the embolic coil is progressively reduced in coil diameter.

At least a portion of the proximal portion of the embolic coil can have a uniform coil diameter from one end to the other end.

The embolic coil can be comprised of a core and a cover layer formed to cover a surface of the core, with a portion or the whole of at least one of the core and the cover layer being made of a ferromagnetic material as a major material.

The core can be made of the ferromagnetic material while the cover layer is made of a material having body tissue compatibility.

The electromagnet can be provided with a coil provided inside the distal end portion of the elongate body.

The electromagnet can comprise a core provided inside the coil.

The core can be formed integrally in one-piece with the elongate body.

The axis of the coil can be aligned with the axis of the distal end portion of the elongate body.

In addition, the elongate body can be made as a wire or tube.

According to another aspect, an elongate medical body for delivering a helical embolic coil into an aneurysm comprises an elongate flexible body possessing a distal end portion adapted to receive the helical embolic coil, and an electromagnet disposed at the distal end portion of the elongate flexible body. The electromagnet is operable in a first state to generate a magnetic attractive force at the distal end portion of the elongate body to hold the helical embolic coil at the distal end of the flexible body through magnetic attraction and in a second state to release the helical embolic coil from being held on the distal end portion of the elongate body.

BRIEF DESCRIPTION OF THE DRAWING FIGURES

DETAILED DESCRIPTION

Figure 1:
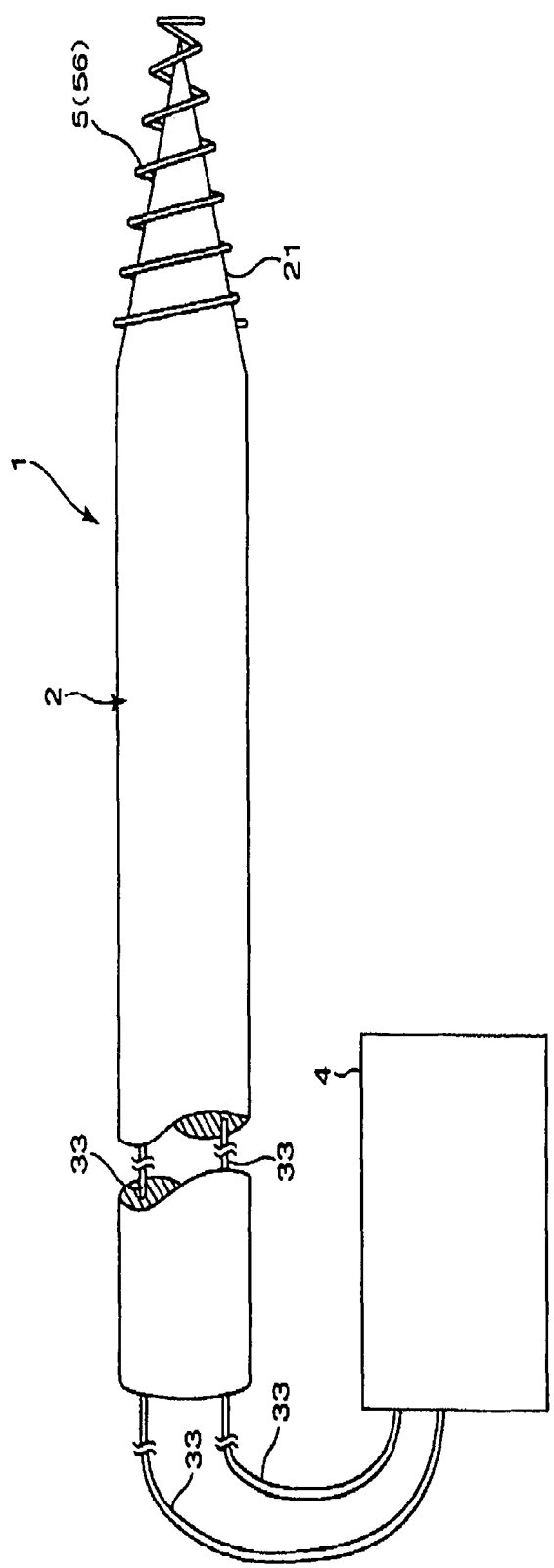
FIG. 1 is a lateral view of a elongate medical device according to one disclosed embodiment.

For convenience, in the description below, the right and the left in FIGS. 1 through 7 are referred to as "the distal end" and "the proximal end", respectively. Also, to facilitate an understanding, in FIGS. 1 thorough 7, the elongate medical body is reduced in longitudinal length and schematically illustrated by magnifying the thickness-wise extent of the medical elongate body. Thus, it is to be understood that the ratio of the length-wise and the thickness-wise dimensions illustrated in the drawing figures is not intended to be an accurate depiction of the actual relative dimensions. Examples of the elongate medical body include an elongate medical wire in which a wire is a main body of the elongate medical body and a medical tube in which a tube is a main body of the elongate body.

The following describes an embodiment in which an elongate medical wire constitutes the elongate medical body.

FIG. 1 illustrates one disclosed embodiment of medical device 1 used to deliver (and retrieve) a helical embolic coil 5 to (from) an aneurysm. The medical device 1 is adapted to be inserted into, for example, the lumen of a catheter (including an endoscope) to supply the spiral or helical embolic coil 5 to the aneurysm of a blood vessel. This medical device 1 includes the elongate wire body 2 which is a main body of an elongate body, an electromagnet 3 (shown in more detail in FIG. 2) provided at the distal end portion 21 of the wire main body 2, and the helical or spiral embolic coil 5). A power supply circuit 4 is connected to the electromagnet 3 to supply power to the electromagnet 3. The power supply circuit 4 supplies power to the electromagnet 3 to thereby produce a magnetic field at the distal end portion 21 of the wire main body 2. As described later, the embolic coil 5 of this disclosed embodiment is comprised of a wire having a primary spiral (helix) with a relatively smaller diameter and elongate in form, and a distal end portion having a secondary spiral (helix) with a relatively larger diameter. Also, it is to be understood that FIGS. 1, 2, 4, 5 and 7 illustrate only the proximal end portion (magnetically attracting portion) of the embolic coil 5 and do not illustrate the remainder of the coil (i.e., the portion of the coil on the distal end side of the magnetically attracting proximal portion).

As described in more detail below, the wire main body 2 permits attachment or detachment of the magnetically attractable proximal end portion 56 of the spiral embolic coil 5 to or from the distal end portion 21 of the main body 2 by switching or changing the power supply state of the power supply circuit 4.

The full length of the wire main body 2 is not particularly restrictive, but is preferably from about 200 to about 5000 mm.

The wire main body 2 possesses flexibility (plasticity or elasticity) and is comprised of a wire rod 22 and a cover layer 23 covering the outer surface of the wire rod 22.

The wire rod 22 is circular in transverse cross-section, although such cross-sectional shape of the wire rod 22 is not particularly limited. By way of example, the wire rod 22 can also possess an oval or quadrangular (particularly, rectangular) cross-section.

The constituent material forming the wire rod 22 is not particularly restrictive, though a flexible or elastic material may preferably be used. Examples of the constituent material of the wire rod 22 include various metal materials such as stainless steel (e.g., SUS304, SUS303, SUS316, SUS316L, SUS316J1, SUS316J1L, SUS405, SUS430, SUS434, SUS444, SUS429, SUS430F, SUS302, and other SUS materials), a piano wire, cobalt-based alloys, alloys having pseudo-elasticity (including a super-elasticity alloy) and resin materials. Among them, alloys which are pseudo-elastic alloys (including super-elastic alloy) are preferable and the super-elastic alloys are more preferable.

A super-elastic alloy is relatively flexible and restorative, but is not likely to undergo plastic deformation or permanent deformation. If the wire rod 22 is made of a super-elastic alloy, the wire main body 2 has sufficient flexibility and restorative characteristics relative to bending, and possesses improved capability of following complicatedly curving and bending blood vessel to provide more excellent operability. In addition, even if the wire main body 2 is repeatedly subjected to curving and bending deformations, it does tend to maintain a bent configuration because of the inherent restorative nature or ability of the wire rod 22. Thus, it is possible to avoid deterioration in the operability of the wire which would otherwise result if the wire main body 2 tended to maintain a bent condition or experience plastic deformation during the use of the medical device 1.

Pseudo-elastic alloys include ones having any shapes of tension-based stress-strain curves, ones in which transformation points such as As, Af, Ms and Mf are clearly measured or not, and ones that are largely deformed (distorted) by stress and substantially restored to the original shapes by removal of the stress.

Examples of preferable compositions of a super-elastic alloy include Ni—Ti-based alloys such as a Ni—Ti alloy of 49 to 52 at. % Ni, a Cu—Zn alloy of 38.5 to 41.5 wt % Zn, a Cu—Zn—X alloy of 1 to 10 wt % X (X is at least one of Be, Si, Sn, Al and Ga) and an Ni—Al alloy of 36 to 38 at. % Al.

A cobalt-based alloy formed into a wire has a high degree of elasticity and an appropriate elastic limit. Thus, a wire made of a cobalt-based alloy has excellent torque transmissibility and is not as likely to cause a problem such as buckling or the like. Any cobalt-based alloy may be used as long as it contains Co as a constituent element. However, it is preferable to use a cobalt-based alloy containing Co as a chief ingredient (i.e., a Co-based alloy in which the content of Co in weight-ratio is highest amongst the elements constituting the alloy). A Co—Ni—Cr-based alloy may more preferably be used. The use of alloys having such compositions makes the effect described above further remarkable. Alloys having such compositions have a high elastic coefficient and can be cold-formed while having a high elastic limit. With the high elastic limit, the alloy having such compositions can be reduced in diameter while still being well suited to sufficiently preventing the occurrence of buckling. Consequently, it can have flexibility and rigidity sufficient to be inserted into a desired region.

Preferable examples of a Co—Ni—Cr-based alloy include an alloy having a composition of 28 to 50 wt % Co-10 to 30 wt % Ni-10 to 30 wt % Cr-remnant Fe; a Co—Ni—Cr-based alloy in which a part thereof (i.e., one or more of the elements Co, Ni or Cr) is substituted or replaced with another element (substitutional element). Providing the substitutional element as a substitute for another element allows the wire main body to exhibit an effect inherent in the substitutional element. The strength of the wire main body 2 can be further enhanced by including, as a substitutional element, at least one selected from the group consisting of Ti, Nb, Ta, Be and Mo. If an element other than Co, Ni and Cr is contained in the alloy, it is preferred that the element (the entire substitutional element) have a content of 30 wt % or less.

A portion of each of the materials or elements Co, Ni and Cr may be substituted with another element. For instance, Mn may be substituted for part of the Ni, thus further improving, for example, the workability. Also, Mo and/or W may be substituted for part of the Cr, thus leading to a further improvement in the elastic limit. A Co—Ni—Cr—Mo-based alloy containing Mo is particularly preferable among Co—Ni—Cr-based alloys.

Examples of specific compositions of a Co—Ni—Cr-based alloy include: (1) 40 wt % Co-22 wt % Ni-25 wt % Cr-2 wt % Mn-0.17 wt % C-0.03 wt % Be-remnant Fe, (2) 40 wt % Co-15 wt % Ni-20 wt % Cr-2 wt % Mn-7 wt % Mo-0.15 wt % C-0.03 wt % Be-remnant Fe, (3) 42 wt % Co-13 wt % Ni-20 wt % Cr-1.6 wt % Mn-2 wt % Mo-2.8 wt % W-0.2 wt % C-0.04 wt % Be-remnant Fe, (4) 45 wt % Co-21 wt % Ni-18 wt % Cr-1 wt % Mn-4 wt % Mo-1 wt % Ti-0.02 wt % C-0.3 wt % Be-remnant Fe, (5) 34 wt % Co-21 wt % Ni-14 wt % Cr-0.5 wt % Mn-6 wt % Mo-2.5 wt % Nb-0.5 wt % Ta-remnant Fe. The phrase Co—Ni—Cr-based alloy as used in at least this disclosed embodiment includes, as examples, the examples of alloys listed above.

The average outer diameter of the wire rod 22 is not particularly limited, though is preferably from about 0.1 to about 0.3 mm.

The cover layer 23 is formed to cover the respective outer surfaces of the wire rod 22 and/or the electromagnet 3. In the illustrated version shown in FIG. 2, the cover layer 23 covers the respective outer surfaces of the wire rod 22 and the electromagnet 3.

The constituent material forming the cover layer 23 is not particularly restrictive. The cover layer 23 may be made of a resin material and a metal material, preferably a material having body tissue compatibility.

The cover layer 23 can be formed to achieve various purposes. One of the purposes is to reduce the friction (sliding resistance) of the medical device 1 to thus improve its sliding performance and thereby enhance the operability of the medical device 1.

To reduce the friction (sliding resistance) of the medical device 1 (main body portion 2), it is preferred that the cover layer 23 be made of a material that can reduce friction as described in more detail below. This reduces the frictional resistance between the embolic coil 5 and the wire main body 2 to enhance sliding performance. Thus, the embolic coil 5 can be prevented from being firmly fixed to the distal end portion 21 of the wire main body 2. In addition, this can help facilitate attachment of the embolic coil 5 to the distal end portion 21 and detachment of the embolic coil 5 from the distal end portion 21. Also, the frictional resistance (sliding performance) of the inner wall of a catheter used together with the medical device 1 (wire main body 2) is reduced to improve the sliding performance, thus making the operability of the medical device 1 (wire main body 2) in the catheter more satisfactory. Because of the reduced sliding performance of the medical device 1 (wire main body 2), the medical device 1 (wire main body 2) can be more reliably prevented from kinking (bending over) or twisting when moved and/or turned in the catheter.

Examples of materials capable of reducing the friction include: polyolefin such as polyethylene and polypropylene, polyvinyl chloride, polyester (PET, PBT, etc.), polyamide, polyimide, polyurethane, polystyrene, polycarbonate, a silicone resin, a fluorine series resin (PTFE, ETFE, etc.) and a complex material thereof.

Among these materials, a fluorine series resin (or a complex material containing this resin) is used to reduce the frictional resistance between the embolic coil 5 and the wire main body 2 to improve sliding performance. This can help prevent the embolic coil 5 from being firmly fixed to the distal end portion 21 of the wire main body 2 and can also facilitate the attachment and detachment of the embolic coil 5 to and from the distal end portion 21. The frictional resistance (sliding resistance) between the medical device 1 (wire main body 2) and the inner wall of the catheter can be reduced more effectively to improve sliding performance. Thus, the operability of the medical device 1 (wire main body 2) is made more satisfactory in the catheter. Because of this, the medical device 1 (wire main body 2) can be more reliably prevented from kinking (bending over) or twisting when moved and/or turned in the catheter.

If a fluorine series resin (or a complex material containing this resin) is used, the cover layer 23 can be put on the wire rod 22 with the resin material heated by baking, spraying or other methods. This can help improve the adhesiveness of the cover layer 23.

If the cover layer 23 is made of a silicone resin (or a complex material containing the silicone resin), it can be formed (it covers the electromagnet 3 or wire rod 22) without heating to be closely-attached reliably and firmly. That is to say, if the cover layer 23 is made of a silicone resin (or a complex material containing a silicone resin), a reactive-curable material or the like can be used and so the cover layer 23 can be formed at room temperature. In this way, the cover layer 23 can be formed at room temperature and so the coating can be performed easily.

The cover layer 23 (particularly, the distal end portion thereof can be provided for the purpose of enhancing safety encountered in inserting the medical device 1 into a blood vessel or the like. For this purpose, it is preferred that the cover layer 23 be made of a flexible material (soft material, elastic material).

Examples of such a flexible material include: polyolefin such as polyethylene and polypropylene, polyvinyl chloride, polyester (PET, PBT, etc.), polyamide, polyimide, polyurethane, polystyrene, a silicone resin, thermoplastic elastomer such as polyurethane elastomer, polyester elastomer, polyamide elastomer and the like, and rubber materials such as latex rubber, silicone rubber and the like, and a complex material combining two or more of them.

In particular, with the cover layer 23 made of the above-mentioned thermoplastic elastomer or rubber materials, the flexibility of the distal end portion of the medical device 1 (wire main body 2) is further enhanced, and the inner wall of a blood vessel can be reliably prevented from being hurt or damaged when the medical device 1 is inserted, thereby providing improved safety.

The cover layer 23 described above may be a laminated body having two or more layers. In addition, the cover layer 23 may be such that the distal end side and the proximal end side are formed of the same material or of different materials. For example, the cover layer 23 may be formed of the flexible material (soft material, elastic material) described above at a portion corresponding to the distal end of the wire main body 2 and the friction-reduced material described above at a portion corresponding to the proximal end side of the wire main body 2. This leads to the coexistence of the improvement of the sliding performance (operability) and improvement of the safety.

In addition, the outer circumferential surface of the wire rod 22 or the like may be subjected to a process (e.g., roughening, chemical treatment, thermal treatment or the like) for improving the adherence of the cover layer 23, or an intermediate layer may be provided to improve the adherence of the cover layer 23.

Fillers (particles) made of a material (the above-mentioned radiopaque material or the like) having contrast performance are dispersed in the cover layer 23 to form a contrast portion.

It is preferred that the outer surface of at least the distal end portion of the wire main body 2 be coated with a hydrophilic material. In the present embodiment, the portion of the outer circumferential surface of the wire main body 2 corresponding to a region extending from the distal end of the wire main body 2 to the vicinity of the proximal end of the wire main body 2 is coated with the hydrophilic material. The hydrophilic material upon becoming moistened provides a lubricating property which reduces the frictional resistance between the embolic coil 5 and the wire main body 2 to improve the sliding performance. This helps prevent the embolic coil 5 from being firmly fixed to the distal end portion 21 of the wire main body 2. In addition, attachment and detachment of the embolic coil 5 to and from the distal end portion 21 is facilitated. The medical device 1 (wire main body 2) is reduced in friction (sliding resistance) to improve sliding performance. Consequently, the operability of the medical device 1 can be enhanced.

Examples of the hydrophilic material include: a cellulosic high-molecular material, polyethylene oxide high-molecular material, maleicacidanhydride (e.g. maleicacid anhydride copolymer such as methylvinylether-maleicacidanhydride) acrylamide-based high-molecular material (e.g. polyacrylamide, block copolymer of polyglycidylmethacrylate-dim-ethylacrylamide (PGMA-DMAA), water-soluble nylon, polyvinyl alcohol, and polyvinylpyrrolidone.

The average thickness of the cover layer 23 is appropriately determined taking into consideration the purpose of forming the cover layer 23, the constituent materials, the formation method and the like. The average thickness of the cover layer 23 is not particularly limited, though is preferably from about 1 to about 100 µm in general. If the thickness of the cover layer 23 is too thin, the purpose for providing the cover layer 23 is not sufficiently exhibited in some cases and the cover layer 23 is more likely to exfoliate. If the thickness of the cover layer 23 is too thick, the physical property of the medical device 1 (main body portion 2) may be affected and the cover layer 23 may exfoliate.

The distal end portion 21 of the wire main body 2 described above has a tapered portion which is progressively reduced in outer diameter toward the distal end of the wire main body. This can help prevent the embolic coil 5 from being inadvertently removed toward the distal end side when the distal end portion 21 is pressed forward in a blood vessel with the embolic coil 5 positioned at the distal end portion 21 of the wire main body 2. The embolic coil 5 can be smoothly disengaged from the distal end portion 21 and can be more easily implanted at a desired position in the aneurysm while giving a patient a relatively low burden.

The length of the tapered portion is not limited to a particular dimension, but is preferably from about 2 to about 3 mm.

The taper angle (the reduction ratio of the outer diameter) of the tapered distal end portion 21 included in the wire main body 2 is preferably different from the taper angle of the embolic coil 5 described later. This reduces a contact area between the distal end portion 21 and the embolic coil 5 at the time of engagement (adhesion) of the distal end portion 21 with the embolic coil 5. Thus, the embolic coil 5 can be prevented from being firmly fixed to the distal end portion 21 of the wire main body 2. In this case, the taper angle (the reduction ratio of the outer diameter) of the tapered distal end portion 21 included in the wire main body 2 is preferably larger than the taper angle of the embolic coil 5 described later. This can more reliably prevent the embolic coil 5 from being firmly fixed to the distal end portion 21 of the wire main body 2 while facilitating the attachment and detachment of the embolic coil 5 to and from the distal end portion 21. In addition, the proximal end portion 56 of the embolic coil 5 is contracted in the axial direction by a magnetic force at the time of the adhesion and then is released (expanded) when the magnetic attraction fore is removed. In this way, the embolic coil 5 can be released. The taper angle (the reduction ratio of the outer diameter) of the tapered distal end portion 21 of the wire main body 2 may be uniform along the tapered portion in the longitudinal direction of the wire main body 2. Alternatively, the distal end portion 21 may have a portion varying in taper angle along the longitudinal direction. For instance, the distal end portion 21 may be formed such that a portion having a relatively large taper angle (the reduction ratio of the outer diameter) and a portion having a relatively small taper angle are repeated alternately.

If the distal end portion 21 is such that the embolic coil 5 can be stably secured thereto, the length and outer diameter of the distal end portion 21 may be set so that the taper angle of the tip of the distal end portion 21 is zero (i.e., is not reduced in outer diameter).

Preferably, the tip surface of the distal end portion 21 is rounded. This can prevent the distal end portion 21 from hurting or damaging the inner wall of the blood vessel even if the embolic coil 5 is not secured to the distal end portion 21.

The average outer diameter of the wire main body 2 (a portion excluding the distal end portion 21) is not particularly limited, but is preferably from about 0.3 to about 0.4 mm.

The electromagnet 3 functions to generate a magnetic field by being energized by the power supply circuit 4. The electromagnet 3 in the present embodiment includes a core 31 provided on the distal side of the wire rod 22 and a coil 32 wounded around the outer circumference of the core 31.

The core 31 is made as a ferromagnetic body as a major material. The core 31 thus configured is positioned inside the coil 32 to increase the magnetic field produced by the electromagnet 3. The axis of the coil 32 and the axis of the elongate main body 2 (and the axis of the core 31) are preferably the same, meaning that the embolic coil 5 and the elongate main body 2 (and the axis of the core 31) are preferably coaxial with one another.

The core 31 is tapered so that its outer diameter is progressively reduces in a direction towards the distal end of the core 31. This makes it possible to generate a magnetic field suitable for the operation (securing/holding and releasing) of the embolic coil 5 as described in more detail below.

It is preferable to integrally form the core 31 with the wire main body 2 (specifically, the cover layer 23 and the wire rod 22) to form a one-piece unitary construction. This makes it possible to increase the mechanical strength of the medical device 1.

The coil 32 is spirally wound along the outer circumferential surface of the core 31. Also, the coil 32 wound around the outer circumference of the core 31 is progressively reduced in coil diameter towards the distal end. This makes it possible to increase the magnetic field resulting from the electromagnet 3 and to generate a magnetic field suitable for the operation (securing and releasing) of the embolic coil 5 described later.

The coil 32 described above is covered by the cover layer 23 at the distal end portion 21 of the wire main body 2. In other words, the coil 32 is provided inside the distal end portion 21 of the wire main body 2. This makes it possible to reduce the size of the distal end portion of the medical device 1, which can reduce a burden on a patient.

The axis of the coil 32 is substantially aligned with the axis of the distal end portion 21 of the wire main body 2. This helps facilitate the generation of a magnetic field that is relatively uniform in the circumferential direction of the medical device 1 to thereby enhance the operability of the medial wire 1.

The coil 32 is connected to the power supply circuit 4 via lines 33, which are preferably positioned between the wire rod 22 and the cover layer 23 in the wire main body 22.

The surfaces of the coil 32 and the lines 33 are each provided with a cover layer (not shown) made of an insulating material. Thus, the coil 32 and lines 33 are insulated from the wire rod 22 and the cover layer 23. It is not necessary to form such an insulating cover layer on the respective surfaces of the coil 32 and lines 33 in the case where a cover layer made of an insulating material is provided on the outer circumferential surface of the wire rod 22 and the inner circumferential surface of the cover layer 23, or in the case where the wire rod 22 and cover layer 23 are made of an insulating material.

The power supply circuit 4 can be configured to be switchable between different states in which current is supplied to the coil 32 of the electromagnet 3 and current is not supplied to the coil 32 of the electromagnet 3. More specifically, the power supply circuit 4 is switchable between two states to effect energization and de-energization of the coil 32. Thus, when the coil 32 is energized, an electric field is generated by the electromagnet 3. When the coil 32 is de-energized, the occurrence of a magnetic field by the electromagnet 3 is stopped.

Alternatively, power supply circuit 4 can be configures so that during energization of the coil 32, the power supply circuit 4 switches the direction of the current flowing to the coils 32. Thus, the power supply circuit 4 is switchable between two different states to switch the directions of the magnetic field 3, namely the polarities of the electromagnet 3.

Figure 3:
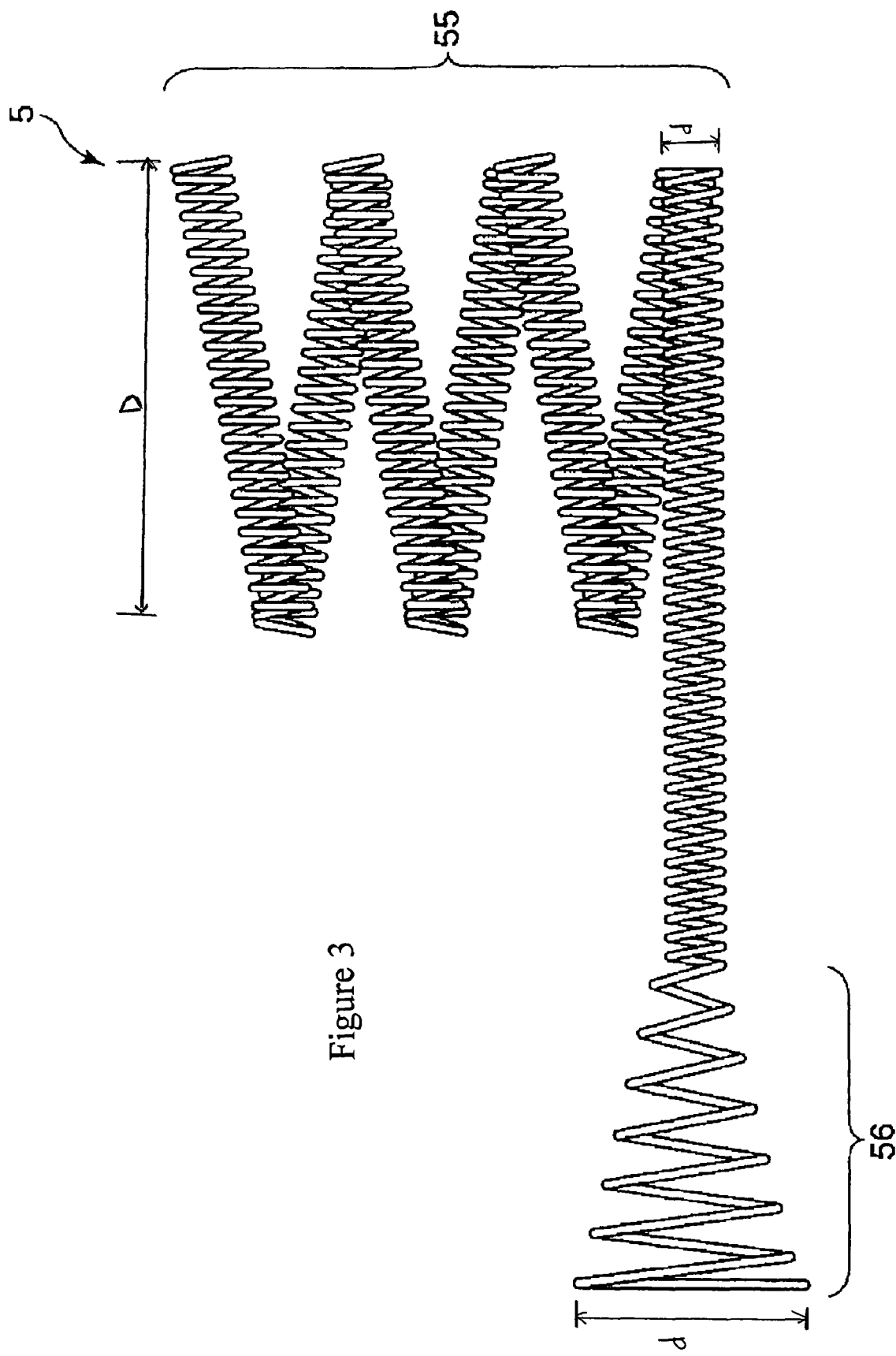
FIG. 3 is an enlarged lateral view illustrating a configurational example of an embolic coil used with, for example, the elongate medical device illustrated in FIG. 1.

The embolic coil 5 is adapted to engage or be secured to the distal end portion 21 of the wire body 2 through magnetic attraction. More specifically, as shown in FIG. 3, the embolic coil 5 is composed of an elongated wire having a primary spiral with a relatively smaller diameter (d) and a secondary spiral portion 55 with a relatively larger diameter (D) at a distal end portion of the coil. The proximal end portion 56 of the embolic coil 5 is formed as a ferromagnetic body to enable magnetic adhesion attraction. Thus, the embolic coil 5 can be magnetically attracted and secured to the distal end portion 21 of the wire main body 2.

The ferromagnetic body forming the proximal end portion 56 of the embolic coil 5 can be formed either as a non-magnetized ferromagnetic body or as a magnetized ferromagnetic body.

If the ferromagnetic body forming the proximal end portion 56 of the embolic coil 5 is a non-magnetized ferromagnetic body, energization of the coil 32 causes the magnetic force of the electromagnet 3 to secure or attach the proximal end portion 56 of the embolic coil 5 to the distal end portion 21 of the wire body 2. On the other hand, de-energization of the coil 32 (i.e., when the coil is not energized) causes the proximal end portion 56 of the embolic coil 5 to be released from the distal end portion 21 so that the coil 5 is no longer secured or attached to the distal end portion 21 of the wire body 2, If the ferromagnetic body forming the proximal end portion 56 of the embolic coil 5 is a magnetized ferromagnetic body, the energization of the coil 32 with current flowing in one direction results in an attraction between the magnetic force of the proximal end portion 56 of the embolic coil 5 and the magnetic force of the electromagnet 3 that secures or attaches the proximal end portion 56 of the embolic coil 5 to the distal end portion 21 through magnetic attraction. Application of current opposite in direction to that at the time of securing or attaching results in a polarity of the electromagnet 3 opposite to that at the time of securing or attaching. This results in a repulsive or repelling action between the magnetic force of the proximal end portion 56 of the embolic coil 5 and the magnetic force of the electromagnet 3 that releases the embolic coil 5 from the distal end portion 21 so that the embolic coil 5 is no longer secured to the distal portion 21 of the wire body through magnetic attraction.

Thus, if the ferromagnetic body forming the proximal end portion 56 of the embolic coil 56 is magnetized, the magnetic force of the proximal end portion 56 (the ferromagnetic body) of the embolic coil 5 causes the proximal end portion 56 of the embolic coil 5 to be secured or attached to the distal end portion 21 upon energization of the coil 32 with current flowing in one direction. The energization of the coil 32 with current flowing in the opposite direction creates a repulsive force between the magnetic force of the electromagnet 3 and the magnetic force of the proximal end portion 56 (the ferromagnetic body) of the embolic coil 5 to release from the distal end portion 21 the embolic coil 5 from the distal end portion 21.

Figure 2:
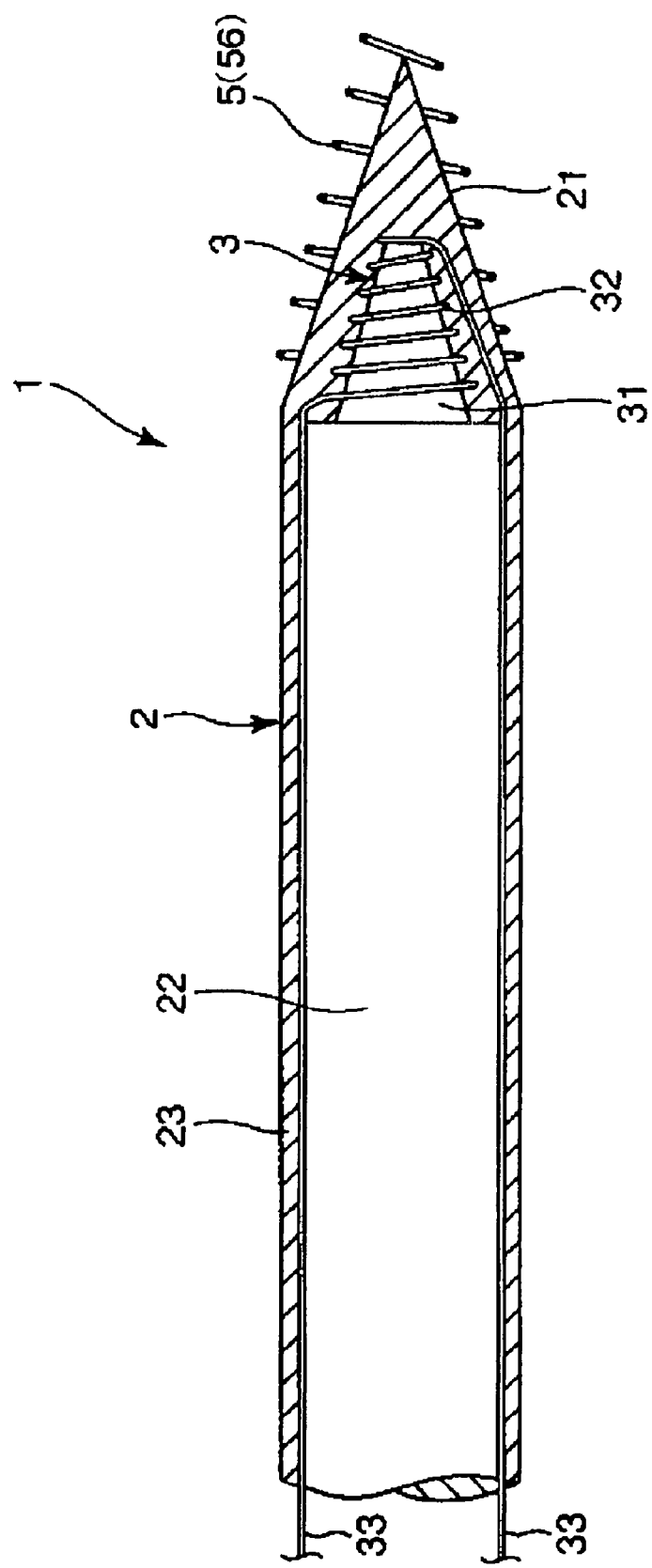
FIG. 2 is a longitudinal cross-sectional view of the elongate medical device illustrated in FIG. 1.

The proximal end portion 56 of the embolic coil 5 may be uniform in coil diameter or may be progressively reduced in coil diameter from its one end to the other end. If the proximal end portion 56 of the embolic coil 5 is progressively reduced in coil diameter such as shown in FIGS. 2 and 3, the proximal end portion can be secured to the outer circumferential surface of the distal end portion 21 of the wire main body 2 which possesses a tapered shape. In this way, when the distal end portion 21 of the wire main body 2 is moved in a blood vessel 21 with the embolic coil 5 attached to the proximal end portion 21 of the wire main body 2, the embolic coil 5 is less likely to inadvertently contact the wall surface of the blood vessel. Also in this regard, the burden on the patient can be reduced. When the embolic coil 5 is moved in a catheter or in a blood vessel with the embolic coil 5 held to the distal end portion 21 of the wire main body 2, a contact area of the surface of the embolic coil 5 with the inner wall of the catheter or with the surface of a living body is significantly reduced. This can reduce sliding resistance, with the result that the operability of the medical device 1 is further improved.

Figure 8:
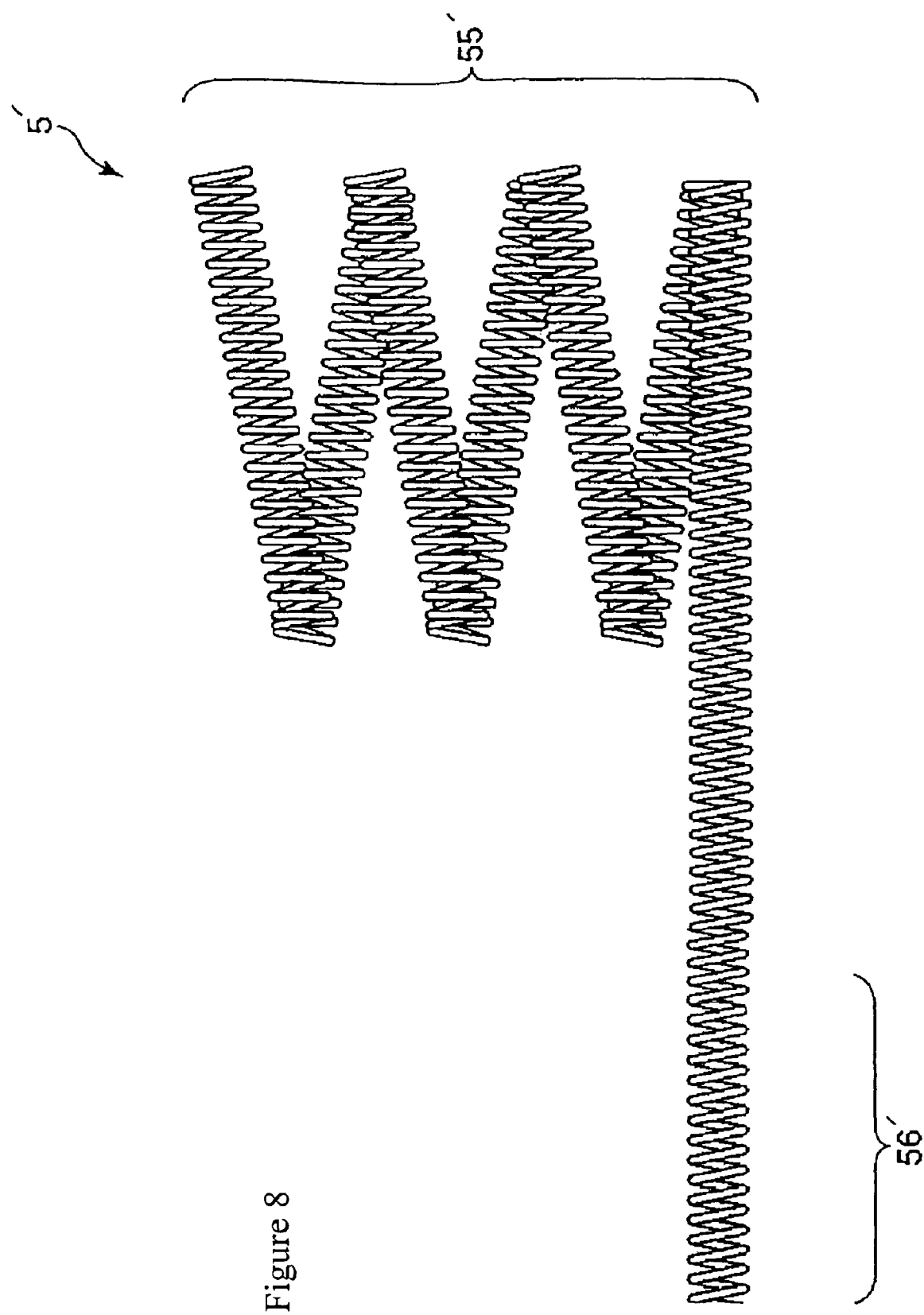
FIG. 8 is a side view of an elongate medical device according to an alternative configuration.

As mentioned above, the proximal end portion 56 of the embolic coil 5 may have a uniform or constant coil diameter instead of the progressively reduced coil diameter. FIG. 8 illustrates an embolic coil 5' possessing a proximal end portion 56' of uniform or constant coil diameter.

Figure 9:
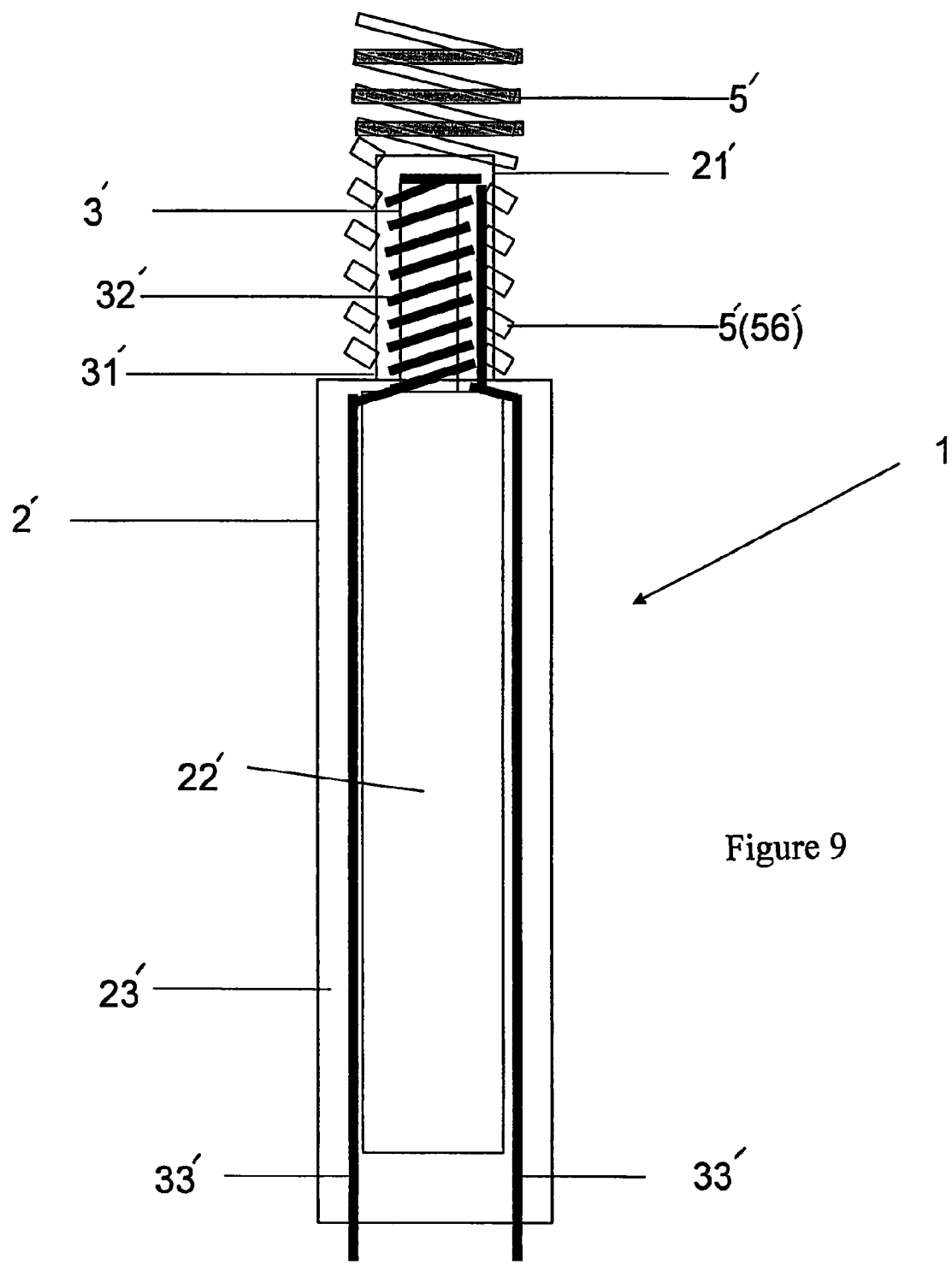
FIG. 9 is an enlarged lateral view illustrating another example of an embolic coil used with, for example, the elongate medical device illustrated in FIG. 8.

In connection with the embolic coil shown in FIG. 8, the distal end portion of the wire main body can be configured with a constant or uniform outer diameter rather than the tapering outer shape shown in FIG. 2. FIG. 9 illustrates an alternative form of the elongate main body 2' possessing a distal end portion 21' whose outer diameter is constant or uniform to magnetically attract the proximal end portion 56' of the embolic coil 5 shown in FIG. 8. Other parts of the elongate main body similar to those previously described above are identified with the same reference numeral, except with the prime (') designation.

Set forth below is a description of several examples of the proximal end portion 56 of the embolic coil 5.

First Example

Figure 4:
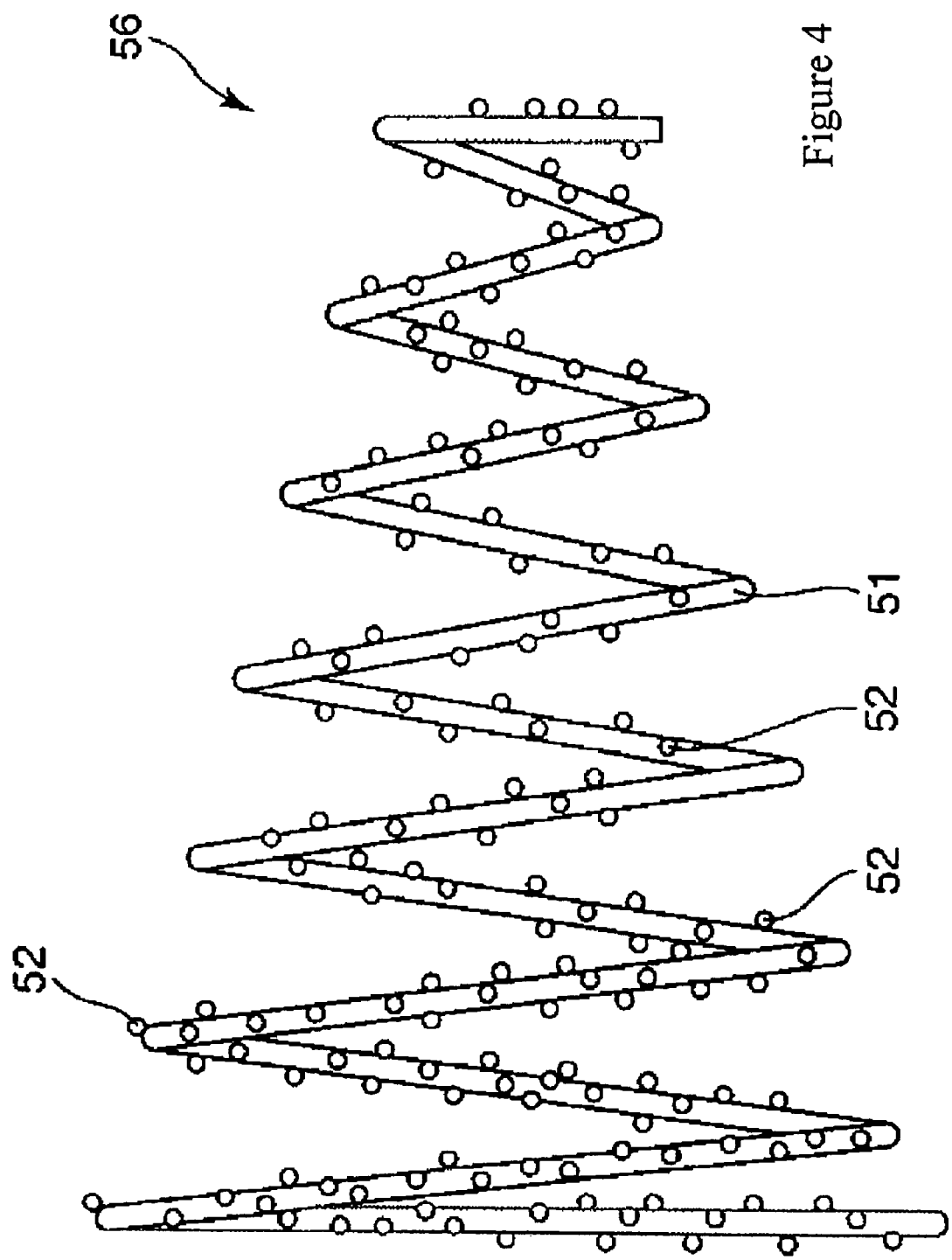
FIG. 4 is an enlarged lateral view illustrating an example of the proximal end portion of the embolic coil illustrated in FIG. 3.

A proximal end portion 56 of an embolic coil 5 in a first example shown in FIG. 4 includes a coil main body 51 and a large number of particulates 52 carried or retained on the coil main body 51, with the particulates 52 each made of a ferromagnetic material as a major material. This causes the embolic coil 5 to be capable of being magnetically attracted. Appropriately distributing the particulates 52 on the coil main body 51 can impart to the embolic coil 5 configured as above a desired magnetic characteristic, thereby allowing the electric field from the electromagnet 3 to provide the desired behavior of the embolic coil 5. FIG. 4 only illustrates the proximal end portion 56 of the embolic coil 5 and omits an illustration of the portion of the embolic coil on the distal end side of the proximal end portion 56 (i.e., the secondary coil portion 56).

The constituent material forming the coil main body 51 is not limited to a particular material. However, the coil main body 51 can use the same constituent material as that of the wire rod 22 or the cover layer 23 described earlier. The coil main body 51 is preferably made of chemically stable constituent materials such as a cobalt-base alloy, metal (radiopaque material) such as tantalum, tungsten, iridium, gold or platinum, or alloy containing them (e.g. a platinum-iridium alloy). In particular, if the coil main body 51 is made of a radiopaque material which does not substantially permit penetration of radioactive rays such as X-rays, the distal end portions of the embolic coil 5 and wire main body 2 provide contrast performance. Thus, they are capable of being inserted into a living body while confirming the position of the distal ends under radiation-ray illumination.

The ferromagnetic material used for the constituent material of the particulates 52 is not particularly restrictive. Examples include metal such as Fe, Co, Ni, or Gd or an alloy containing one or more of such materials.

Second Example

Figure 5:
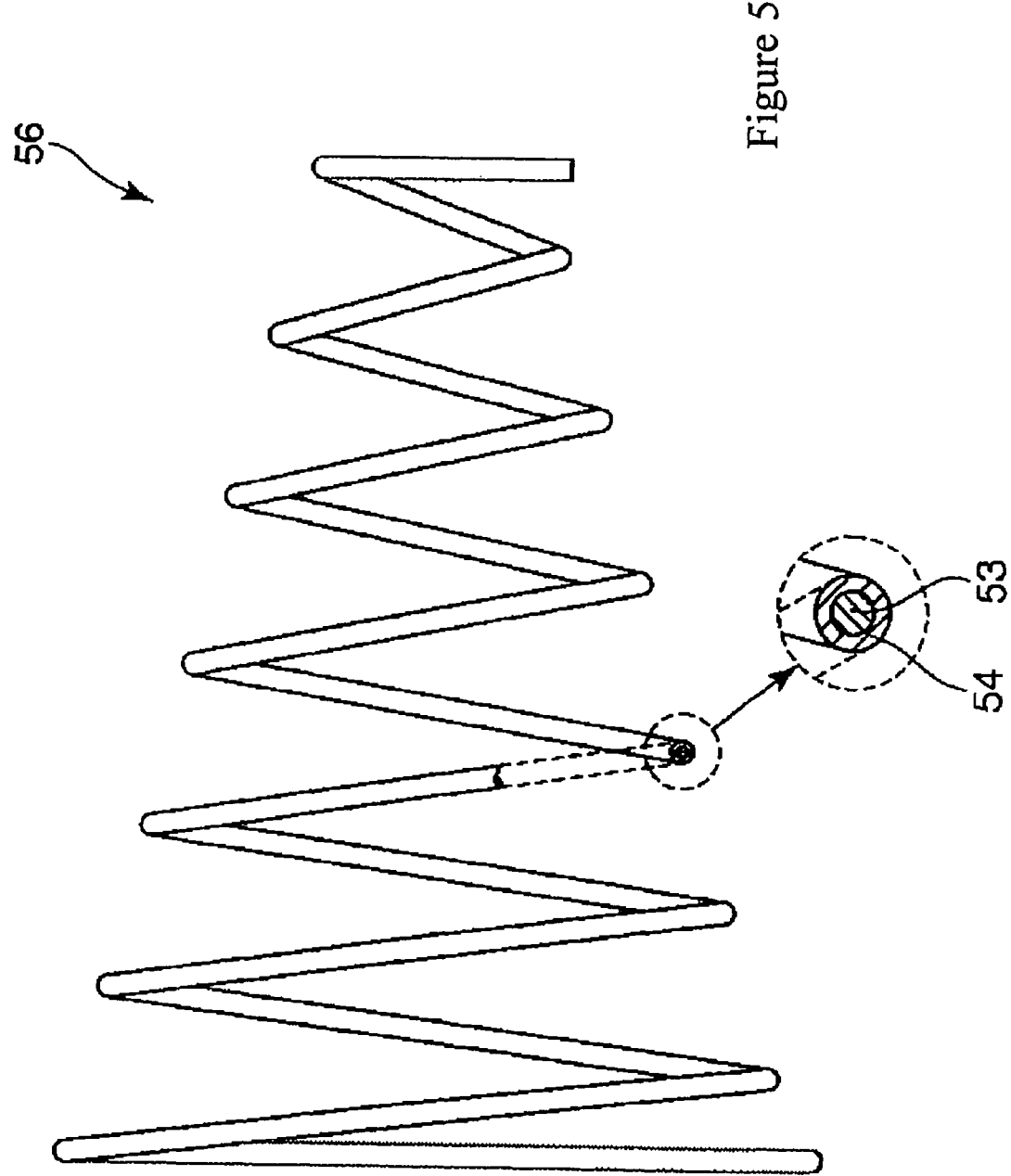
FIG. 5 is an enlarged cross-sectional view illustrating another example of the proximal end portion of the embolic coil shown in FIG. 3.

An embolic coil 5 according to a second example shown in FIG. 5 includes a core 53 and a cover layer 54 covering the surface of the core 53. FIG. 5 illustrates only the proximal end portion 56 of the embolic coil 5 and omits an illustration of the portion of the embolic coil on the distal end side of the proximal end portion 56 (i.e., the secondary coil portion 56).

At least one of the core 53 and cover layer 54 is formed of a ferromagnetic body as a major material. By appropriately selecting the constituent materials of the core 53 and the cover layer 54, desired characteristics can be imparted to the embolic coil 5 so that the embolic coil 5 is capable of being magnetically attracted.

For instance, if the core 53 is made of the ferromagnetic material mentioned above as a major material and the cover layer 54 is made of a material having body tissue compatibility, the resulting embolic coil 5 will possess quite good living body compatibility while also being magnetically attractable.

The material having living tissue compatibility is not particularly limited as long as it is relatively highly safe with respect to a living body. Examples of material to be used preferably include chemically stable materials such as a cobalt-base alloy, metal such as tantalum, tungsten, iridium, gold or platinum, or an alloy containing them (e.g. a platinum-iridium alloy). If the core 53 or cover layer 54 is made of a radiopaque material such as a noble metal which does not substantially permit penetration of radioactive rays such as X-rays, the distal end portions of the embolic coil 5 and wire main body 2 provide contrast performance and can be inserted into a living body while confirming the position of the distal end under radiation-ray illumination.

Also an intermediate layer can be provided between the core 53 and the cover layer 54. If the core 53 and the cover layer 54 are each made of metal for instance, the intermediate layer is an alloy layer or oblique alloy layer containing such metal. Such an alloy layer or oblique alloy layer can be formed by heat treatment with the cover layer 54 formed on the core 53. This can enhance durability of the embolic coil 5. The term oblique alloy generally refers to an alloy comprised of at least two materials (metals) whose composition forms a gradient locationally. For example, when distal and proximal portions, and an intermediate portion between the distal and proximal portions, exist, and the property (material) of the distal and proximal portions differs, the property (material) of the intermediate portion forms a gradient from the distal portion to the proximal portion.

The cover layer 54 of the embolic coil 5 can be omitted depending on the constituent material of the core 53.

The secondary spiral portion 55 is located on the distal side of the proximal end portion 56, the latter of which, as described above, possesses magnetically attractable characteristics. The portion of the coil 5 forming the secondary spiral portion 55 is preferably spiraled as shown in FIG. 3, meaning that the distal portion of the coil is wound to form a spiral. The secondary spiral portion 55 can be deformable so as to be inserted into a microcatheter. That is, the secondary spiral portion 55 is preferably adapted to be inserted into a microcatheter, and upon being inserted into the microcatheter is deformed linearly along the inner wall of the microcatheter. Upon being released or removed from the microcatheter, the secondary spiral portion 55 is again restored to the relatively larger diameter spiral form mentioned above and shown in FIG. 3. Alternatively, the secondary spiral portion can be configured to possess, when not inside the microcatheter, a three-dimensionally complicated shape generally conforming to the internal shape of the aneurysm in which the secondary spiral portion is to be implanted. Thus, the embolic coil 5 can be relatively stably implanted in the aneurysm.

While the secondary spiral portion 55 illustrated in FIG. 3 possesses a uniform coil diameter, the secondary spiral portion may also be configured to have a progressively reduced or increased coil diameter in a direction toward the proximal end side from the distal end side.

The constituent material of the secondary spiral portion 55 is not particularly limited. By way of example, it is possible to use the same material as that of the proximal end portion 56 mentioned earlier.

The secondary spiral portion 55 does not need to be formed of a material providing magnetically attractive properties. While the constituent material of the secondary spiral portion 55 may be the same as or different from that of the proximal end portion 56, it is preferred that the secondary spiral portion 55 be made of a material that is not magnetically attractable. This makes it possible to relatively easily and reliably secure or hold just the proximal end portion 56 of the embolic coil 5 to the distal end portion 21 of the wire main body 2.

To enable confirmation of the positional relationship between the distal end portion 21 of the wire main body 2 and the embolic coil 5 under radiation-ray illumination, at least one portion of each of the distal end portion 21 (more specifically, the wire rod 22 or cover layer 23) of the wire main body 2 and the embolic coil 5 may be made of a material having contrast performance (e.g. a radiopaque material such as mentioned earlier). This helps enhance the operability of the medical device 1.

Figure 7A:
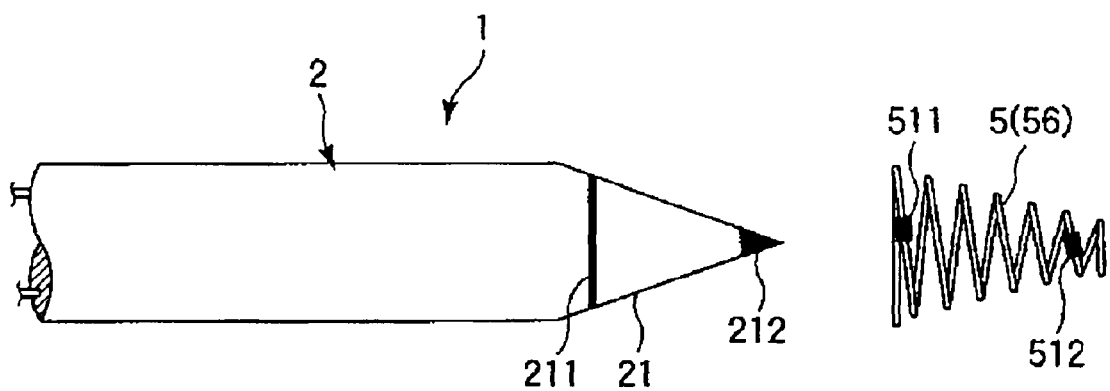
FIGS. 7A and 7B are lateral views of an elongate medical device according to another embodiment of the present invention.
Figure 7B:
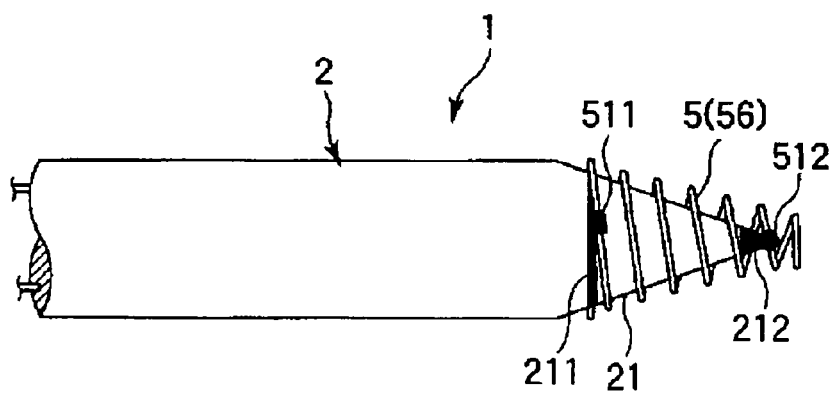

FIG. 7A illustrates one example in which the wire main body 2 is provided with two contrast portions (radiopaque markers) 211, 212 spaced axially apart from each other at the distal end portion 21. In addition, the embolic coil 5 is provided with at least two contrast portions (radiopaque markers) 511, 512 spaced axially apart from each other at intervals corresponding to the two contrast portions 211 and 212, respectively. Referring to FIG. 7B, the contrast portions 211, 212, 511, 512 are arranged as described below. When the embolic coil 5 is accurately attached to the distal end portion 21 of the wire main body 2, the contrast portion 211 on the proximal side of the distal portion 21 of the wire main body 2 is superposed on (generally axially and circumferentially aligned with) the contrast portion 511 on the proximal side of the embolic coil 5. In addition, the contrast portion 212 on the distal side of the distal portion 21 of the wire body 2 is superposed on (generally axially and circumferentially aligned with) the contrast portion 512 on the distal side of the embolic coil 5. In this way, it is possible to visually confirm, under radiation-ray illumination, whether or not the embolic coil 5 is accurately attached to the distal end portion 21 of the wire main body 2. The embolic coil 5 can be effectively released in a simple and reliable way in the state in which it has been accurately attached to the distal end portion 21 of the wire main body 2. Consequently, the operability of the medical device 1 is enhanced.

As described above, the medical device 1 is configured such that the magnetically attachable spiral embolic coil 5 is attached and detached to and from the distal end portion 21 by switching or changing the energization states of the coil 32.

Set forth below is a description of an example of how the medical wire configured as above can be used.

Figure 6A:
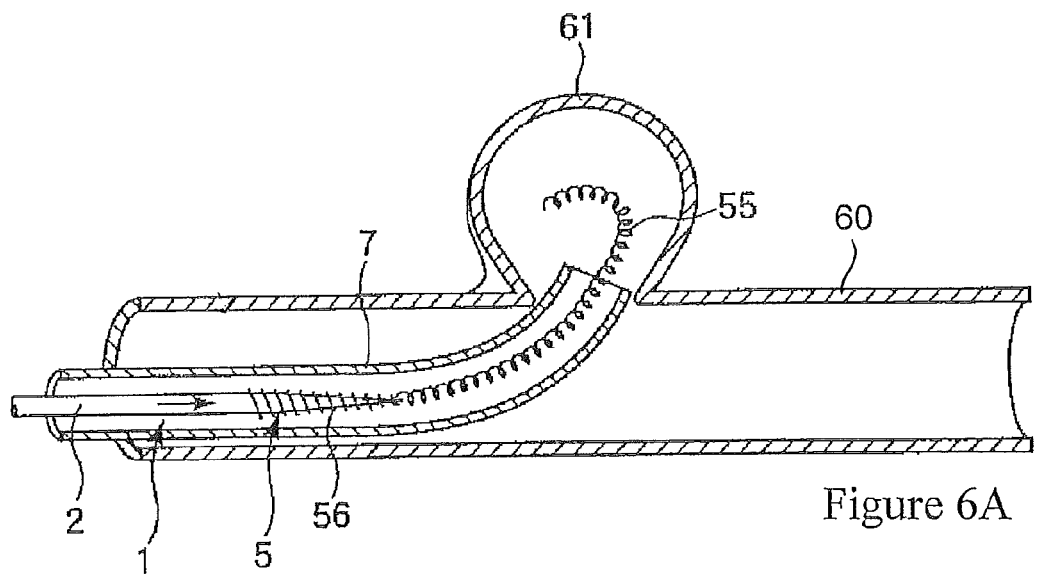
FIGS. 6A, 6B and 6C are diagrams generally illustrating aspects of a procedure which can be employed using the elongate medical device illustrated in FIG. 1.

In a state where a guide wire (not shown) is inserted into a microcatheter 7, at first, the guide wire is advanced to the desired position in a blood vessel. The microcatheter 7 is then advanced along the guide wire and is inserted into the blood vessel 60. While being guided by the guide wire, the microcatheter is advanced toward the distal end of the guide wire. The distal end of the microcatheter 7 is positioned in an aneurysm 61 as shown in FIG. 6A. Thereafter, the guide wire is removed from the microcatheter 7. In the state in which the embolic coil 5 (more specifically, the magnetically attractable proximal end portion 56) is secured to or held on the outer circumference of the distal end portion 21 of the wire main body 2, the distal end portion 21 of the main body portion 2 of the medical device 1 is inserted into the microcatheter 7 as shown in FIG. 6A.

The embolic coil 5 is secured to or held on the outer circumference of the distal end portion 21 of the wire body 2 through magnetic attraction. A more specific explanation of this attachment of the embolic coil 5 to the distal end portion 21 of the wire body is described below.

If the ferromagnetic body forming the distal end portion 56 of the embolic coil 5 is not magnetized, energization of the coil 32 causes the electromagnet 3 to generate a magnetic field. In this state, the proximal end portion 56 of the embolic coil 5 is held or secured to the distal end portion 21 by the magnetic force of the electromagnet 3.

If the ferromagnetic body forming the distal end portion 56 of the embolic coil 5 is magnetized, energization of the coil 32 causes the electromagnet 3 to generate a magnetic field. In this state, with the current flowing in one direction, a magnetic attractive force is created between the proximal end portion 56 of the embolic coil 5 and the electromagnet 3 to hold or secure the proximal end portion 56 of the embolic coil 5 to the distal end portion 21 of the wire body 2.

Alternatively, if the ferromagnetic body forming the proximal end portion 56 of the embolic coil 5 is magnetized and the distal end portion 21 of the wire main body 2 and the core 31 are made of a magnetically attractable material, the coil 32 is de-energized, that is, the electromagnet 3 is made to not generate a magnetic field. In this state, the magnetic force of the proximal end portion 56 (the magnetized ferromagnetic body) of the embolic coil 5 causes the proximal end portion 56 of the embolic coil 5 to be attracted and secured to the distal end portion 21.

The secondary spiral portion 55 of the embolic coil 5 positioned in the microcatheter 7 is restricted in shape by the inner wall of the microcatheter 7 so that the secondary spiral portion extends generally linearly along the microcatheter 7.

Figure 6B:
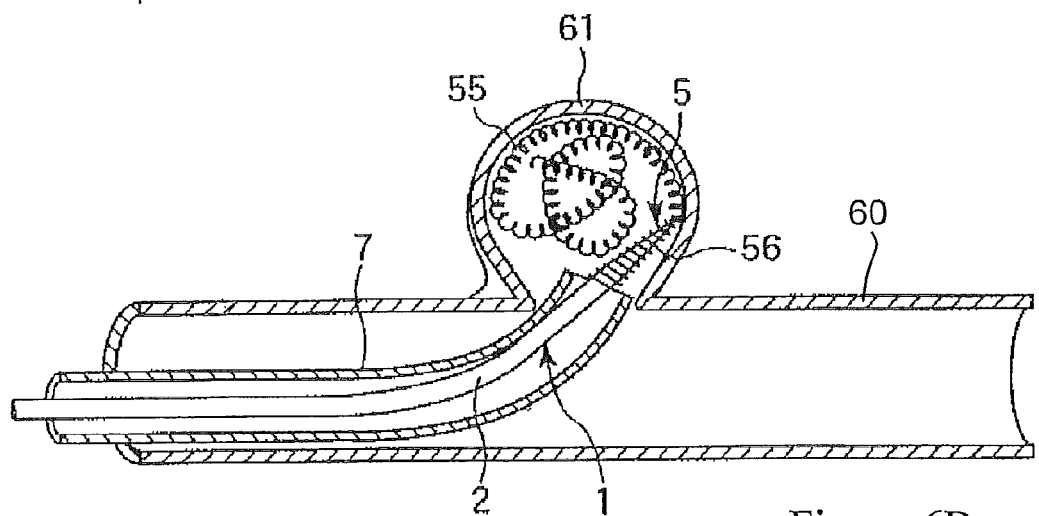

While maintaining the state in which the proximal end portion 56 of the embolic coil 5 is secured or held to the distal end portion 21 of the wire main body 2 by magnetic attraction, the distal end portion 21 is advanced in the distal direction. As shown in FIG. 6B, the distal end portion 21 of the wire main body 2 is advanced to project from (beyond) the distal end of the microcatheter 7 and to project inside the aneurysm 61 through the opening of the aneurysm 61.

At this time, the secondary spiral portion 55 of the embolic coil 5 positioned outside the microcatheter 7 and inside the aneurysm 61 changes in shape so as to be restored generally towards it original shape (the spiral shape). FIG. 6B illustrates the state in which the secondary spiral portion 55 is not restored to the original spiral shape but to a three-dimensionally complicated shape generally conforming to the shape of the inner wall of the aneurysm 61.

Figure 6C:
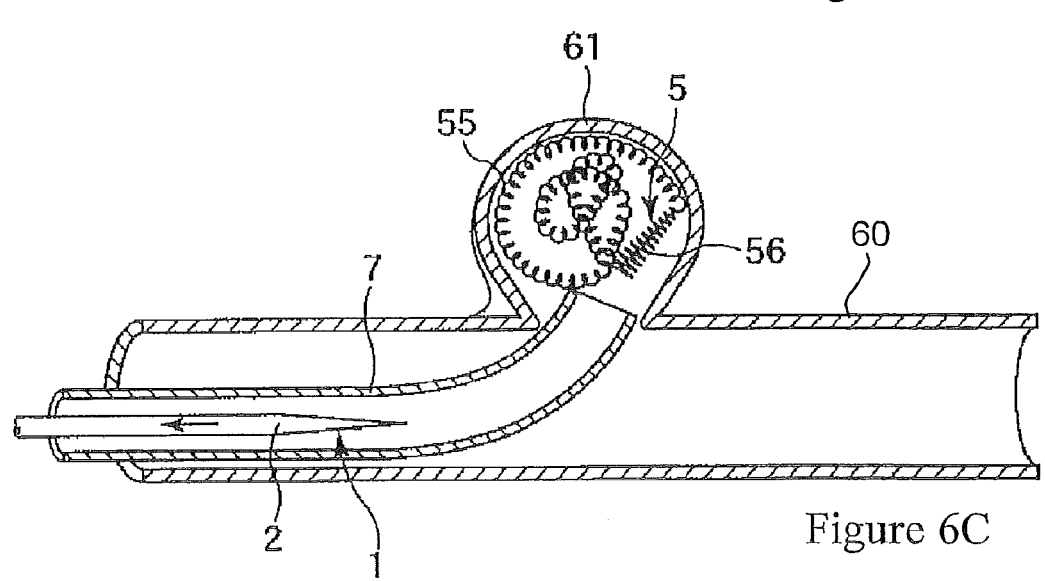

Next, the embolic coil 5 is released from the distal end portion 21 of the wire main body 2 (i.e., the magnetically attractive force is cancelled or removed) and the wire main body 2 is withdrawn into the microcatheter 7 and removed while leaving behind the embolic coil 5. Thus, as shown in FIG. 6C, the embolic coil 5 is supplied to and filled in the aneurysm 61.

As discussed above, the proximal end portion 56 of the embolic coil 5 is released from the distal end portion 21 of the wire main body 2 once the embolic coil 5 is positioned as desired (e.g., in the aneurysm). If the ferromagnetic body forming the proximal end portion 56 of the embolic coil 5 is not magnetized, the release of the attachment of the proximal end portion 56 of the embolic coil 5 from the distal end portion 21 of the wire body 2 is accomplished by de-energizing the coil 32 to thus remove the magnetic attractive force.

On the other hand, if the ferromagnetic body forming the proximal end portion 56 of the embolic coil 5 is magnetized, current opposite in direction to that at the time of securing (holding) the proximal end portion 56 is applied to the coil 32 to change the polarity of the electromagnet 3 to a direction opposite to that at the time of the attraction/securing. This creates a repulsive or repelling action between the magnetic force of the proximal end portion 56 of the embolic coil 5 and the magnetic force of the electromagnet 3, thus releasing the embolic coil 5 from the distal end portion 21.

Otherwise, if the ferromagnetic body forming the proximal end portion 56 of the embolic coil 5 is magnetized and the distal end portion 21 of the wire main body 2 and the core 31 are made of a magnetically attractable material, energization of the coil 32 causes the repulsive or repelling action between the magnetic force of the electromagnet 3 and the magnetic force of the proximal end portion 56 (the ferromagnetic body) of the embolic coil 5 to release the embolic coil 5 from the distal end portion 21.

Thus, as described above, the energization state of the power supply circuit 4 is switched to cancel or release the attraction of the embolic coil 5 to the distal end portion 21, thus changing from a state or condition in which the embolic coil is held or secured (magnetically attracted) to the distal end portion 21 to a state or condition in which the embolic coil 5 is no longer held or secured (not magnetically attracted) to the distal end portion 21.

As described above, the release of the magnetic attraction action between the electromagnet 3 and the proximal end portion 56 (the ferromagnetic body) of the embolic coil 5 causes the proximal end portion 56 of the embolic coil 5 secured or held to the distal end portion 21 to be released from the distal end portion 21. At this time, the embolic coil 5 which has been moved through a blood vessel can be implanted (deposited) at a position on the distal side of the distal end portion 21. Thus, even if the distal end portion 21 can be inserted only part of the way into the aneurysm 61 because, for example, the aneurysm 61 has a relatively large depth or for other reasons, the embolic coil 5 can be supplied to a desired position in the aneurysm 61.

The proximal end portion 56 of the embolic coil 5 is axially contracted by a magnetic force at the time of magnetic attraction and then is expanded upon releasing the embolic coil 5. Also in this way, the embolic coil 5 can be supplied to and implanted at a position on the further distal side of the distal end portion 21.

Thus, the medical device 1 described here is adapted to supply and implant the embolic coil 5 in the aneurysm 61.

The medical device 1 described here is adapted to attach and detach the embolic coil 5 to and from the wire main body 2 in response to the energization state of the power supply circuit 4. Thus, even after the embolic coil 5 has once been implanted, the implanted embolic coil can be removed or recovered by inserting the main body portion 2 into a blood vessel, and advancing the main body portion 2 in the blood vessel to bring the distal end portion 21 of the wire main body 2 close to the implanted proximal end portion 56 of the embolic coil 5 (e.g., inserting the distal and portion 21 of the wire body 2 into the proximal end portion 56 of the embolic coil 5) for once again achieving magnetic attraction. Once the embolic coil 5 is held to the wire main body 2 by magnetic attraction in one of the ways described above, the main body portion 2 can be moved along the blood vessel in a direction away from the aneurysm to remove the embolic coil from the aneurysm.

When the embolic coil 5 is attached to or detached from the wire main body 2, a material having a harmful effect on a human body does not flow out and also in this regard the burden on the patient is reduced. Thus, a medical device or apparatus having a relatively high safety is thus provided.

The elongate medical device has been described with reference to the embodiment illustrated in the drawing figures. However, the medical device is not specifically limited to the embodiment illustrated and described herein. Portions or aspects of the elongate medical device can be replaced with other components configured to exhibit the same or similar functions. In addition, features can be added to the medical device described above.

For instance, the shape of the main body of the elongate device and the main body of the embolic coil are not limited to those of the embodiment described above.

Thus, it is to be understood that the principles, preferred embodiments and other disclosed aspects have been described in the foregoing specification. However, the invention which is intended to be protected is not to be construed as limited to the particular embodiment disclosed. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An elongate medical device comprising:
   a flexible elongate body possessing a distal end portion;
   an electromagnet disposed at the distal end portion of the elongate body;
   the electromagnet possessing a proximal end, a distal end and a tapering outer diameter portion at which the outer diameter of the electromagnet decreases towards the distal end of the electromagnet;
   the electromagnet being energizable to generate a magnetic field at the distal end portion of the elongate body;
   a helical embolic coil made of ferromagnetic material mounted on the distal end portion of the elongate body, the helical embolic coil possessing a tapering proximal end portion having a tapering shape at which the inner diameter of the proximal end portion of the embolic coil decreases towards a distal end of the embolic coil, the proximal end portion of the helical embolic coil possessing the tapering shape before the helical embolic coil is mounted on the distal end portion of the elongate body, a proximal-most end of the helical embolic coil being open to permit the distal end portion of the elongate body to be inserted into the tapering proximal end portion of the helical embolic coil;
   the tapering proximal end portion of the helical embolic coil being mounted on the distal end portion of the elongate body so that the distal end portion of the elongate body is positioned inside the tapering proximal end portion of the helical coil, the tapering proximal end portion of the helical embolic coil and the tapering outer diameter portion of the electromagnet axially overlapping one another, and the tapering outer diameter portion of the electromagnet magnetically attracting the tapering proximal end portion of the helical embolic coil to secure the helical embolic coil to the distal end portion of the flexible elongate body in one energization status of the electromagnet, and releasing magnetic attraction of the tapering proximal end portion of the helical embolic coil by changing the energization status of the electromagnet to be different than the one energization status.

2. The elongate medical device of claim 1, wherein the proximal end portion of the embolic coil is formed of ferromagnetic material, the tapering proximal end portion of the embolic coil being magnetically attracted to the distal end portion of the elongate body to secure the embolic coil to the elongate body by energizing the electromagnet, the tapering proximal end portion of the embolic coil being released from magnet attraction to the distal end of the elongate body by discontinuing the energization of the electromagnet.

3. The elongate medical device of claim 1, wherein the proximal end portion of the embolic coil is formed of ferromagnetic material, the tapering proximal end portion of the embolic coil being magnetically attracted to the distal end portion of the elongate body to secure the embolic coil to the elongate body by energizing the electromagnet, the tapering proximal end portion of the embolic coil being released from magnet attraction to the distal end of the elongate body by reversing polarity of the electromagnet relative to the polarity of the electromagnet when the tapering proximal end portion of the embolic coil is magnetically attracted to the distal end portion of the elongate body.

4. The elongate medical device of claim 1, wherein the tapering proximal end portion of the embolic coil is formed of ferromagnetic material, the tapering proximal end portion of the embolic coil being magnetically attracted to the distal end portion of the elongate body to secure the embolic coil to the elongate body by discontinuing energization of the electromagnet, and the proximal end portion of the embolic coil being released from magnet attraction to the distal end of the elongate body by energizing the electromagnet.

5. The elongate medical device of claim 1, wherein at least part of the distal end portion of the elongate body is a tapered distal end portion in which an outer diameter of the elongate body progressively reduces toward a distal end.

6. The elongate medical device of claim 1, wherein the tapering proximal end portion of the embolic coil has an outer diameter that is progressively reducing from one end.

7. The elongate medical device of claim 1, wherein the distal end portion of the elongate body is a tapered distal end portion, the tapered distal end portion of the elongate body axially overlapping both the tapering proximal end portion of the helical embolic coil and the tapering outer diameter portion of the electromagnet.

8. The elongate medical device of claim 1, wherein the embolic coil comprises a center core material and a coating layer covering the center core material, and at least one of the center core material or the coating layer being at least partially formed of ferromagnetic material.

9. The elongate medical device of claim 8, wherein the center core material is formed of the ferromagnetic material, and the coating layer is formed of a material having biocompatibility.

10. The elongate medical device of claim 1, wherein the electromagnet comprises a coil disposed inside the distal end portion of the elongate body.

11. The elongate medical device of claim 10, wherein the electromagnet also comprises a magnetic core disposed inside the coil of the electromagnet.

12. The elongate medical device of claim 11, wherein the magnetic core is integrally formed as a unitary body with the elongate body.

13. The elongate medical device of claim 10, wherein the coil of the electromagnet and the elongate body each possess an axis, the axis of the coil of the electromagnet being coaxial with the axis of the elongate body.

14. The elongate medical device of claim 1, wherein the elongate body is a wire or a tube.

15. The elongate medical device of claim 1, wherein the distal end portion of the elongate body is a tapered distal end portion, the tapered distal end portion of the elongate body axially overlapping both the tapering proximal end portion of the helical embolic coil and the tapering outer diameter portion of the electromagnet, the tapered distal end portion of the elongate body being tapered at a first taper angle, and the tapering proximal end portion of the helical embolic coil being tapered at a second taper angle that is different from the first taper angle.

16. The elongate medical device of claim 1, wherein the helical embolic coil includes a distal portion positioned distally of the proximal end portion of the helical embolic coil, the distal portion of the helical embolic coil being spirally wound so that the coil is wound in a spiral.

17. The elongate medical device of claim 16, wherein the inner diameter of the spirally wound distal portion of the helical embolic coil is constant.

18. A method for delivering a helical embolic coil to an interior of an aneurysm comprising advancing an elongate medical device through a blood vessel, the elongate medical device comprising a flexible elongate body possessing a distal end portion, an electromagnet embedded in the distal end portion of the elongate body, and a helical embolic coil at least partially comprised of ferromagnetic material and having a proximal end portion possessing a tapering shape defining a tapering proximal end portion of the helical embolic coil which is mounted on and held on the distal end portion of the elongate body by magnetic attraction created between the electromagnet and the tapering proximal end portion of the helical embolic coil, the electromagnet possessing a proximal end, a distal end and a tapering outer diameter portion at which the outer diameter of the electromagnet decreases towards the distal end of the electromagnet, the helical embolic coil possessing an inner diameter and the tapering proximal end portion of the helical embolic coil having an inner diameter decreasing towards a distal end of the helical embolic coil, the proximal end portion of the helical embolic coil possessing the tapering shape before the helical embolic coil is mounted on the distal end portion of the elongate body, the helical embolic coil possessing a proximal-most end that is open to permit the distal end portion of the elongate body to be inserted into the tapering proximal end portion of the helical embolic coil, the tapering outer diameter portion of the electromagnet being positioned inside the tapering proximal end portion of the helical embolic coil so that the tapering proximal end portion of the helical embolic coil and the tapering outer diameter portion of the electromagnet axially overlapping one another;

the elongate medical device being advanced in the blood vessel to position at least a portion of the helical embolic coil in an aneurysm in the blood vessel;

removing the magnetic attraction between the embolic coil and the helical embolic coil to release the embolic coil from being held on the distal end portion of the elongate body by the magnet attraction; and thereafter moving the elongate body away from the embolic coil to leave the embolic coil in the aneurysm.

19. The method of claim 18, wherein the magnetic attraction holding the embolic coil on the distal end portion of the elongate body is produced by energization of the electromagnet, and wherein the removing of the magnetic attraction between the electromagnet and the embolic coil comprises de-energizing the electromagnet.

20. The method of claim 18, wherein the magnetic attraction holding the embolic coil on the distal end portion of the elongate body is produced by energization of the electromagnet, and wherein the removing of the magnetic attraction between the electromagnet and the embolic coil comprises reversing polarity of the electromagnet relative to the polarity of the electromagnet when the embolic coil is magnetically attracted to the distal end portion of the elongate body.

21. The method of claim 18, wherein the removing of the magnetic attraction between the embolic coil and the embolic coil comprises energizing the electromagnet, and wherein the magnetic attraction holding the embolic coil on the distal end portion of the elongate body is produced by discontinuing energization of the electromagnet.

22. A method for retrieving a helical embolic coil from inside an aneurysm, comprising:

advancing an elongate flexible body, possessing a tapering distal end portion at which an outer diameter of the elongate flexible body decreases toward a distal end portion of the elongate body and an electromagnet embedded in the tapering distal end portion of the elongate body, through a blood vessel to position the distal end portion in an aneurysm in which is located a helical embolic coil, the electromagnet possessing a proximal end, a distal end and a tapering outer diameter portion at which the outer diameter of the electromagnet decreases towards the distal end of the electromagnet, the tapering distal end portion of the elongate flexible body and the tapering outer diameter portion of the electromagnet axially overlapping one another, and wherein the helical embolic coil which is located in the aneurysm while the flexible body is being advanced through the blood vessel toward the aneurysm possesses a tapering proximal end portion at which an inner diameter of the proximal end portion of the embolic coil decreases towards a distal end of the embolic coil, the helical embolic coil possessing a proximal-most end that is open to permit the distal end portion of the elongate body to be inserted into the tapering proximal end portion of the helical embolic coil;

magnetically attracting the embolic coil to the distal end portion of the elongate body through operation of the electromagnet to hold the tapering proximal end portion of the embolic coil on the tapering distal end portion of the elongate body so that the tapering proximal end portion of the embolic coil is positioned inside the tapering distal end portion of the elongate body and axially overlaps the tapering distal end portion of the elongate body; and moving the elongate body within the blood vessel in a direction away from the aneurysm as the tapering proximal end portion of the embolic coil is held on the tapering distal end portion of the elongate body through magnetic attraction to remove the embolic coil from the aneurysm.

23. An elongate medical device comprising:

a flexible elongate body possessing a tapering distal end portion at which the outer diameter of the flexible body decreases towards a distal end of the elongated body;

an electromagnet disposed at the tapering distal end portion of the elongate body;

the electromagnet possessing a proximal end, a distal end and a tapering outer diameter portion at which the outer diameter of the electromagnet decreases towards the distal end of the electromagnet;

the electromagnet being energizable to generate a magnetic field at the tapering distal end portion of the elongate body;

a helical embolic coil made of ferromagnetic material and mounted on the tapering distal end portion of the elongate body;

the helical embolic coil possessing, prior to being mounted on the tapering distal end portion of the elongate body, a tapering proximal end portion at which the inner diameter of the proximal end portion of the embolic coil decreases towards a distal end of the embolic coil;

a proximal-most end of the helical embolic coil being open to permit the tapering distal end portion of the elongate body to be inserted into the tapering proximal end portion of the helical embolic coil; and the tapering proximal end portion of the helical embolic coil being mounted on the tapering distal end portion of the elongate body so that the tapering distal end portion of the elongate body is positioned inside the tapering proximal end portion of the helical coil, the tapering proximal end portion of the helical embolic coil and the tapering outer diameter portion of the electromagnet axially overlapping one another, and the tapering outer diameter portion of the electromagnet magnetically attracting the tapering proximal end portion of the helical embolic coil to secure the helical embolic coil to the tapering distal end portion of the flexible elongate body in one energization status of the electromagnet, and releasing magnetic attraction of the tapering proximal end portion of the helical embolic coil by changing the energization status of the electromagnet to be different than the one energization status.

24. A method for delivering a helical embolic coil to an interior of an aneurysm comprising advancing an elongate medical device through a blood vessel, the elongate medical device comprising a flexible elongate body possessing a tapering distal end portion at which the outer diameter of the flexible body decreases towards a distal end of the elongated body, an electromagnet disposed at the tapering distal end portion of the elongate body, and a helical embolic coil at least partially comprised of ferromagnetic material and having a tapering proximal end portion disposed on the distal end portion of the elongate body and held on the tapering distal end portion of the elongate body by magnetic attraction created between the electromagnet and the helical embolic coil, the helical embolic coil possessing the tapering proximal end portion prior to being disposed on the tapering distal end portion of the elongate body, a proximal-most end of the helical embolic coil being open to permit the tapering distal end portion of the elongate body to be inserted into the tapering proximal end portion of the helical embolic coil, the electromagnet possessing a proximal end, a distal end and a tapering outer diameter portion at which the outer diameter of the electromagnet decreases towards the distal end of the electromagnet, the helical embolic coil possessing an inner diameter and the tapering proximal end portion of the helical embolic coil having an inner diameter decreasing towards a distal end of the helical embolic coil, the tapering proximal end portion of the helical embolic coil and the tapering outer diameter portion of the electromagnet axially overlapping one another;

the elongate medical device being advanced in the blood vessel to position at least a portion of the helical embolic coil in an aneurysm in the blood vessel;

removing the magnetic attraction between the embolic coil and the helical embolic coil to release the embolic coil from being held on the tapering distal end portion of the elongate body by the magnet attraction; and thereafter moving the elongate body away from the embolic coil to leave the embolic coil in the aneurysm.

* * * * *